(12) United States Patent
Sullivan et al.

(10) Patent No.: US 7,214,345 B1
(45) Date of Patent: May 8, 2007

(54) APPARATUS FOR ANALYZING REDUCED INORGANIC SULPHUR

(75) Inventors: Leigh Albert Sullivan, Wollongbar (AU); David Murray McConchie, Goonellabah (AU); Richard Bush, Goonellabah (AU)

(73) Assignee: Risatec Pty Limited, Cammeray, NSW (AU)

( * ) Notice: Subject to any disclaimer, the term of this patent is extended or adjusted under 35 U.S.C. 154(b) by 0 days.

(21) Appl. No.: 09/937,207

(22) PCT Filed: Mar. 22, 2000

(86) PCT No.: PCT/AU00/00224

§ 371 (c)(1),
(2), (4) Date: Sep. 21, 2001

(87) PCT Pub. No.: WO00/57174

PCT Pub. Date: Sep. 28, 2000

(30) Foreign Application Priority Data

Mar. 22, 1999 (AU) .................................. PP9347

(51) Int. Cl.
G01N 31/12 (2006.01)
G01N 21/00 (2006.01)
G01N 33/22 (2006.01)

(52) U.S. Cl. ............... 422/80; 422/82.05; 422/82.09; 436/121

(58) Field of Classification Search ........ 436/119–121, 436/147, 155; 422/50, 52, 68.1, 82.05, 82.12
See application file for complete search history.

(56) References Cited

U.S. PATENT DOCUMENTS 4,141,800 A * 2/1979 Breuer et al. ............ 205/779.5
4,238,198 A * 12/1980 Swaim et al. ............... 436/123
5,080,867 A * 1/1992 Cooke .......................... 422/86
5,935,519 A * 8/1999 Benner et al. ................ 422/52

FOREIGN PATENT DOCUMENTS

JP 08-327625 * 8/1996

OTHER PUBLICATIONS

"Chromium Reducible Sulphur", Laboratory Methods Guidelines, Aug. 1998.
Derwent Abstracts Accession No. 91-162504/22, SU 1578-672 A (GEOCHEM MIN) Jul. 15, 1990.
Derwent Abstracts Accession No. 97-090521/09, M24, JP 08327625 A (Nippon Steel Corp) Dec. 13, 1996.

* cited by examiner

Primary Examiner—Yelena G. Gakh
(74) Attorney, Agent, or Firm—Renner, Otto, Boisselle & Sklar, LLP

(57) ABSTRACT

An apparatus for measuring the reduced inorganic sulfur content of a sample. The apparatus has a reaction chamber (12) and means (14) for introducing a reducing agent that can selectively convert the reduced inorganic sulfur of a sample in the reaction chamber (12) to hydrogen sulfide. The reducing agent can be chromous chloride. The apparatus also includes means for measuring the amount of hydrogen sulfide evolved by reaction of the reducing agent with the sample and a detector for detecting when evolution of the hydrogen sulfide has reduced or ceased. The term "reduced inorganic sulfur" refers to sulfur in a form that can undergo oxidation and includes mineral sulphides and elemental sulfur.

19 Claims, 2 Drawing Sheets

United States Patent US 7,214,345 B1

APPARATUS FOR ANALYZING REDUCED INORGANIC SULPHUR

FIELD OF THE INVENTION

The present invention relates to an apparatus for the quantitative analysis of reduced inorganic sulfur.

BACKGROUND ART

Sulfur is present in the environment in several different forms which may be generally classified as organic and inorganic sulfur. The presence of each form of sulfur has important environmental implications. For example, combustion of both inorganic and organic sulfur produces sulfur dioxide, a greenhouse gas and source of acid rain. Another significant environmental problem is the acid generating potential of a class of inorganic sulfur materials known as reduced inorganic sulfur. These compounds produce acid when materials containing them are mined, excavated or drained, and exposed to atmospheric oxygen. The term "reduced inorganic sulfur" refers to sulfur in a form that can undergo oxidation and includes mineral disulfides (e.g. pyrite and chalcopyrite), monosulfides (e.g. sphalerite, galena and covelline), polysulphides (e.g. pyrrhotite and bornite), non-stoichoimetric metal sulfides (e.g. greigite), other sulphides such as chalcocite, sulfites (salts of sulfurous acids) and elemental sulfur. In the present specification and claims the term "reduced inorganic sulfur" will be understood to include any inorganic sulfur compound that can be oxidised.

Further types of naturally occurring inorganic sulfur compounds are the sulfate minerals, such as gypsum, which include sulfur in the oxidized sulfate form. These materials are generally not a source of acid in the environment.

When sulfide bearing material is mined or excavated, oxidation of the reduced inorganic sulfur may occur. The result is acid sulfate soil and acid mine drainage. Acid mine drainage refers to acid water produced by the oxidation of minerals such as pyrite in the presence of water and is one of the major environmental problems facing the mining industry. The oxidation of reduced inorganic sulfur in acid sulfate soils is a global environmental problem affecting more than 12 million hectares of agricultural land worldwide, degrading aquatic habitats and corroding concrete and steel infrastructure. It is therefore important for environmental management to be able to measure the amount of reduced inorganic sulfur in a wide range of materials including sediments, soils, mine spoil, sludge, petroleum, mineral ores, fossil fuels and water.

There are several known methods for measuring the sulfur content of a material. Combustion followed by measurement of evolved sulfur oxides is used to measure the total sulfur content (i.e. the combined inorganic and organic sulfur). Such methods are typically used to measure the sulfur content of coal. Combustion of coal is a major source of sulfur dioxide pollution. However, the combustion method does not distinguish between organic sulfur, reduced inorganic sulfur or mineral sulfates and accordingly cannot be used to accurately quantify the reduced inorganic sulfur in a sample.

The most widely used method for assaying reduced inorganic sulfur is by peroxide oxidation in which the sulfur is oxidised to sulfate. The amount of sulfate liberated by peroxide oxidation is then analysed by conventional wet chemical quantitative analysis. Although this method is the accepted procedure, the present inventors have surprisingly and unexpectedly observed that the method is subject to serious interferences from organic sulfur and sulfate minerals such as gypsum. This interference is particularly important when sediments having low reduced inorganic sulfur are measured. An erroneous estimate of the reduced inorganic sulfur content may lead to the recommendation of costly and/or inappropriate and environmentally damaging management practices.

Other methods for analysing reduced inorganic sulfur, but which are considered to be less accurate than the peroxide oxidation method, include:

(a) measuring the total sulfur and soluble sulfur content and estimating the reduced inorganic sulfur content from the difference between the two values. A disadvantage of such differential measurement is that the errors are cumulative.
(b) microscopic examination of a sample, and
(c) indirect measurement by estimating the amount of pyritic iron ($FeS_2$) in a sample. However non-pyritic forms of reduced inorganic sulfur are not measured.

It is therefore an object of the present invention to provide a method and apparatus for measuring the reduced inorganic sulfur content of a sample selectively and accurately.

DISCLOSURE OF THE INVENTION

According to a first broad form of the invention there is provided an apparatus for measuring the reduced inorganic sulfur content of a sample, the apparatus having a reaction chamber, means for introducing a reducing agent that can selectively convert the reduced inorganic sulfur of a sample into the reaction chamber to hydrogen sulfide, means for measuring the amount of hydrogen sulfide evolved by reaction of the reducing agent with the sample and a detector for detecting when evolution of the hydrogen sulfide has reduced or ceased.

The apparatus of the present invention has a reaction chamber for allowing a sample to be tested to be digested by a reducing agent that selectively converts the reduced inorganic sulfur component of a sample to $H_2S$. The reducing agent should not react with organic sulfur or sulfate materials to produce $H_2S$. Preferred reducing agents include chromous salts, stannous salts and mercurous salts.

An especially preferred reducing agent is acidified chromous chloride. Acidified chromous chloride solutions are typically prepared by passing acidified chromic chloride through a column containing zinc, pre-amalgamated in mercuric nitrate. This process is difficult, slow and requires specialised equipment to minimise atmospheric oxidation of the acidified $CrCl_2$. Also, acidified $CrCl_2$ is unstable and can only be stored for a few days. Thus, it is preferred that chromous chloride is generated in situ in the reaction chamber. Typically, chromium, concentrated HCl, ethanol and distilled water are introduced into the reaction vessel. The chromium is typically in the form of a powder, but may also be added as a pellet or slurry.

The reduction reaction is typically carried out in an inert atmosphere such as nitrogen or argon, but can for short periods of time be conducted in air, such as up to about 20 minutes. Generally, the reaction is carried out at elevated temperatures with or without agitation under reflux conditions. The condenser used in the reflux process may be cooled by any of the known methods including a continuous flow of water or a refrigeration unit. In a particularly preferred embodiment of the invention, the apparatus includes a condenser that is cooled by means of water that is recirculated through a refrigeration unit. This arrangement allows for the apparatus to be in the form of a portable unit that is suitable for use in the field.

The apparatus of the invention is typically automated and controlled by a central processor which can control some, or essentially all, of the functions of the apparatus. This allows the apparatus to be operated by non-skilled personnel.

Typically, the amounts of reagents added to the reaction chamber are automatically supplied to the reaction chamber in pre-determined quantities in a pre-determined order. Generally, the liquid ingredients are added using a peristaltic pump.

In a further broad form of the present invention there is provided an automated apparatus for measuring the reduced inorganic sulfur content of a sample, the apparatus having a reaction chamber, means for heating the chamber, a condenser, means for introducing a reducing agent into the reaction chamber which converts reduced inorganic sulfur to hydrogen sulfide and measuring means for measuring the amount of hydrogen sulfide evolved. Typically, the apparatus includes a refrigeration unit for cooling water for the condenser.

The reduced inorganic sulfur composition of the sample may be calculated from the amount of $H_2S$ evolved by reaction with the reductant. The $H_2S$ evolution may be measured by any of the known methods of measuring $H_2S$. Such methods include colourimetric, turbidimetric and gravimetric methods. Particularly preferred methods include electrochemical, spectroscopic or chromatographic techniques such as mass spectroscopy, gas chromatography, UV or IR spectroscopy. A particularly preferred measurement means is an electrochemical gas analyser. Generally, the gas which provides the atmosphere in the reaction chamber also serves as a carrier gas to carry the evolved $H_2S$ to the measurement means.

The amount of $H_2S$ evolved may also be measured indirectly. For example, $H_2S$ may be oxidised to sulfate or sulfur dioxide. These oxidation products may then be measured by suitable methods including turbidimetric or gravimetric, chromatographic or spectroscopic methods.

The apparatus of the present invention typically includes a means for detecting when the evolution of $H_2S$ has decreased to a pre-determined rate. Typically, this is when $H_2S$ evolution has substantially ceased. Cessation of $H_2S$ evolution indicates that the reduction reaction has been completed. When completed, a fresh sample may be analysed. With conventional wet chemical procedures, a sample is allowed to react for a pre-determined maximum length of time. The present inventors have observed that the reduction reaction can often take much less time than has traditionally been allowed. Thus, by being able to monitor when the reaction has ceased, sample throughput may be optimised. The apparatus may include an alarm or other signalling device to alert an operator that the reaction has finished. Alternatively and/or in addition to, the apparatus may have means for automatically disengaging any heating of the reaction chamber and deactivate the condenser on completion of the reduction reaction.

The means for detecting when evolution of $H_2S$ has ceased may be in addition to, or part of, the $H_2S$ measuring means. For example a gas sensor or other detection means may be associated with the reaction chamber to detect the $H_2S$ therein. Gas sensors for detecting the presence of $H_2S$ are known.

In the preferred embodiment where the $H_2S$ measurement means is an electrochemical gas analyser or spectrophotometric analyser, the analyser may be programmed to detect when the rate of $H_2S$ evolution has decreased.

Preferably the electrochemical gas analyser can measure the $H_2S$ concentration on a real time basis to allow the rate of $H_2S$ evolution to be constantly monitored. Typically, the $H_2S$ evolution data may be represented as a function of cumulative $H_2S$ concentration v time or absolute $H_2S$ concentration v. time.

Different forms of reduced inorganic sulfur react at different rates. Thus, by being able to monitor the rate of $H_2S$ evolution, information can be obtained as to the relative amounts of different forms of reduced sulfur materials present in the sample.

According to a further broad form of the invention there is provided an apparatus for measuring the amount of reduced inorganic sulfur in a sample, the apparatus having a reaction chamber, a means of introducing a reducing agent that can selectively convert the inorganic reduced sulfur of the sample in the reaction chamber to hydrogen sulfide and means for continually monitoring the amount of hydrogen sulfide evolved.

According to still a further broad form of the invention there is provided a method of measuring the amount of reduced inorganic sulfur in a sample, the method including reacting a sample with a reducing agent that selectively converts the reduced inorganic sulfur to hydrogen sulfide and measuring hydrogen sulfide evolved as a function of time.

The ability to determine the relative amounts of different types of reduced inorganic sulfur is important for environmental management. This enables predictions to be made as to the potential rate of acid generation as opposed to simply calculating the total acid generating potential of a soil material.

A knowledge of a form of sulfur generally referred to as acid volatile inorganic sulfur is of particular importance. Acid volatile sulfur includes monosulfides and non-stoichiometric sulphides such as greigite and mackinawite. In the preferred apparatus in which acidic chromous chloride is generated in situ, the sample can be treated with the concentrated HCl and ethanol only. Neither chromium nor water are added.

Only the acid volatile sulfur fraction will react under these conditions and can thus be selectively analysed. If the total reduced inorganic sulfur is required, the same sample can then be treated with the chromous chloride reductant by introducing chromium powder and water into the reaction chamber as described above.

BEST MODE

Figure 1:
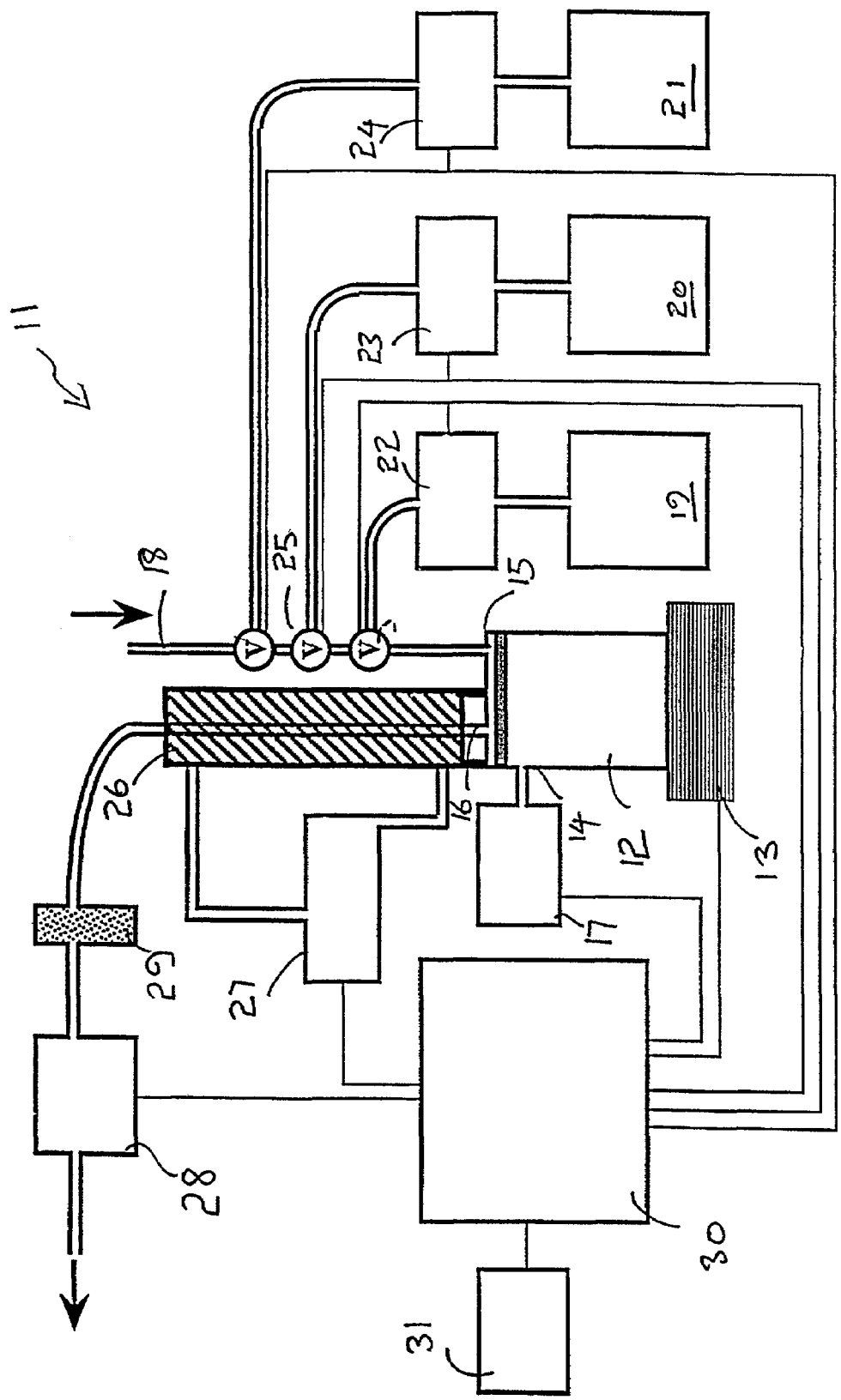
FIG. 1 schematically illustrates a preferred apparatus of the present invention.
Figure 2:
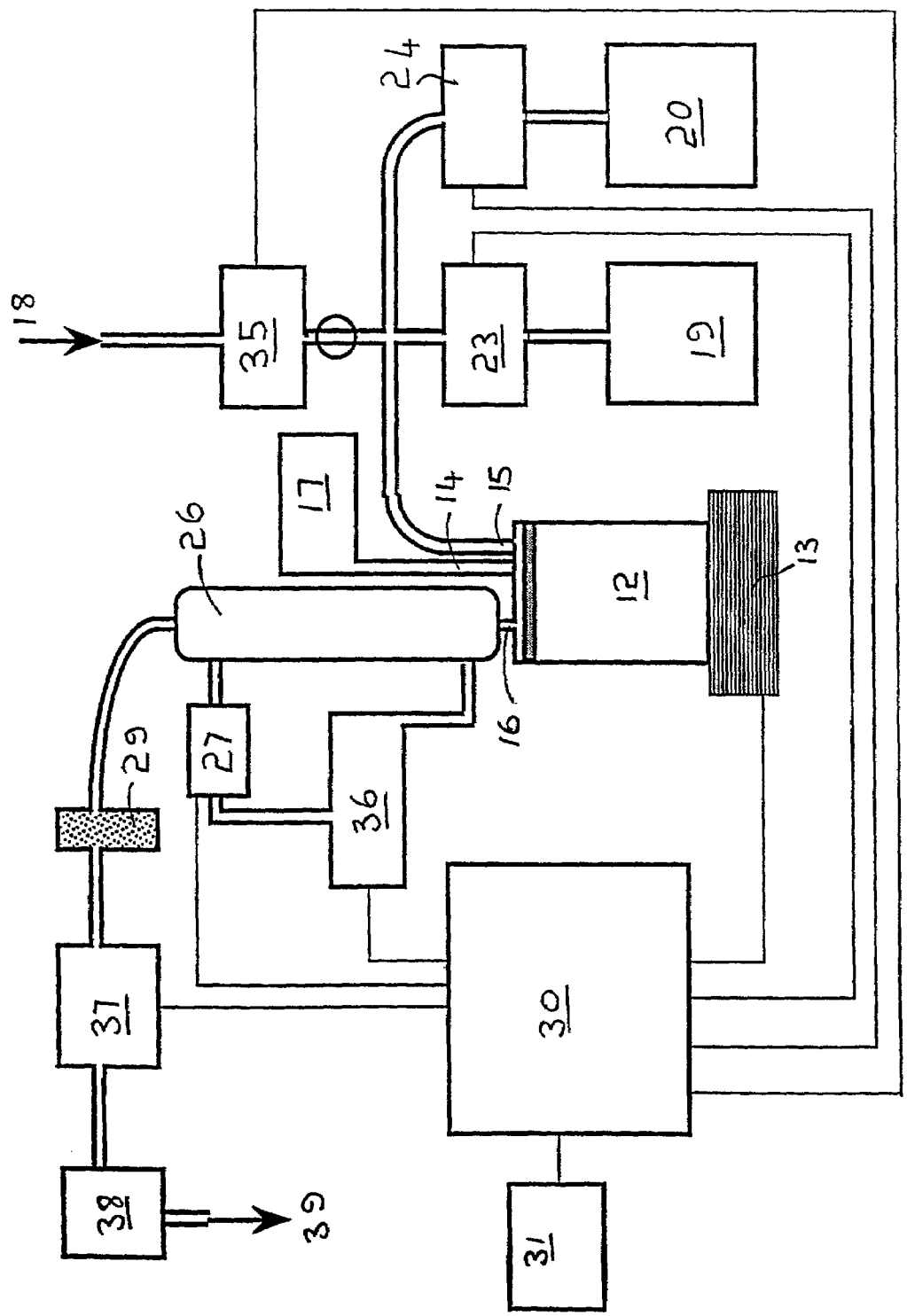
FIG. 2 illustrates a further preferred apparatus of the present invention.

The apparatus of both FIGS. 1 and 2 are designed to be fully automated and to be portable to allow onsite use in the field.

The apparatus 11 illustrated in FIG. 1 has a removable reaction vessel 12. An operator can place a known volume or mass of a sample to be tested into the reaction vessel. Alternatively, the apparatus can include an in-built balance to measure the mass of material in the reaction chamber. The reaction vessel 12 is placed in a heating mantle 13 which is equipped with a magnetic stirrer. In use, the reaction vessel is connected, with an air-tight seal, to inlets 14, 15 and outlet 16. The sealed connection may be provided by any suitable means such as ground glass joints or O ring seals.

The inlet 14 is connected to a chromium powder dispenser 17. The inlet 15 is connected, with an air-tight seal, to a nitrogen gas source 18 and to acid and water and ethanol reservoirs 19, 20. The reservoirs 19, 20, 21 each have a peristaltic pump 22, 23, 24 for delivering pre-determined amounts of liquids via three way valves to inlet 15. The outlet 16 is connected an insulated condenser 26 which typically has copper pipes surrounding a glass core. Refrigerant is supplied to the condenser 26 from pump 27. Typically, the apparatus includes a heat exchange apparatus by which heat extracted from the condenser can be used to heat the mantle 13. The upper end of the condenser 26 is connected, via an air-tight seal, to an IR gas analyser 28. A moisture control unit 29 is disposed between condenser and analyser 28.

The apparatus is operated by a central control computer 30. The power source 31 is typically a 12V power supply. However, mains supply of any voltage (e.g. 110V or 240V), AC or DC, may be used by the incorporation of a suitable adaptor.

To operate the apparatus, an operator places an amount of a sample to be tested in the reaction chamber and places the chamber in the mantle. Prior to analysis, the reservoirs of the chamber are charged with chromium powder, ethanol, water and concentrated HCl respectively. The sample to be tested may be any material containing reduced inorganic sulfur and includes soil, mine spoil, fossil fuels such as coal and oil, sediments, plants and animal materials, water (both naturally occurring and waste), chemical waste and minerals. The samples may be pretreated depending on the nature of the sample. For example the mineral samples may be fine ground prior to analysis.

The apparatus is operated by the computer 30 which can be programmed to fully automate the analysis. If desired manual override capabilities may be included. Under normal operational conditions, all that is required of the operator after placement of the sample in the reaction chamber is to press an "on" switch. This will initiate purging of the system with nitrogen for a predetermined and monitored flow rate. After a fixed time, predetermined amounts of chromium powder, water, ethanol and 12N HCl are added to the reaction chamber in turn. The water also serves to flush the HCl from the lines.

The amounts of reagent added will depend on the weight of the sample. For a 1 g sample, typically about 2.059 g chromium powder, 10 mL ethanol, 28.25 mL of 12N HCl and 31.75 mL of water are added.

After addition of the reagents, the reaction chamber is heated to boiling with stirring. As $H_2S$ is evolved it is carried by the nitrogen through the dessicant in the moisture trap 29 to the IR gas analyser 28. The cumulative concentration of the $H_2S$ gas is calculated by the computer 30 using an algorithm relating $H_2S$ concentration and gas flow rate. When $H_2S$ evolution has ceased or fallen below a predetermined level the computer will terminate the analysis by sequentially disengaging the electrochemical gas analyser, and turning off the heating mantle 13, gas flow and condenser 26. The reaction vessel 12 can then be removed by the operator and cleaned. The apparatus is ready for the next analysis.

The total amount of reduced inorganic sulfur can be read directly from a digital panel or stored digitally. The results may also be presented graphically as either cumulative $H_2S$ production or real time $H_2S$ production rates.

The apparatus of FIG. 2 is similar to that illustrated in FIG. 1 and the same reference numerals refer to the same features.

The apparatus does not include an ethanol reservoir. Ethanol is instead added to reaction vessel 12 together with a sample for analysis. The nitrogen inlet of FIG. 1 has been replaced by a pump 35 to introduce air as the carrier gas. The condenser 26 is cooled by water pumped from refrigeration unit 36 via pump 27. The IR analyser has been replaced by an electrochemical gas analyser 37. A $H_2S$ trap 38 is located between the analyser and vent 39.

The above procedures may be modified to separately analyse the acid volatile sulfur fraction. In this case, the sample and ethanol are placed in the reaction chamber as before, but only HCl (20 mL) is added. The heating mantle is not required and remains turned off. If both the acid volatile and total reduced sulfur are required, the first procedure may then be performed on the sample remaining in the reaction chamber. However, it will only be necessary to add 8.25 mL of HCl (because 20 mL have already been added) plus the chromium powder and water.

It can be seen that the apparatus of the present invention can provide a self contained, portable and automated analyser for reduced inorganic sulfur. At present there is no automated system for quantifying reduced inorganic sulfur. All existing techniques used by industry must be performed by skilled personnel in a well equipped laboratory. Thus, it has hitherto not been possible to analyse reduced inorganic sulfur on site. Automation of the present apparatus allows onsite analysis. Further, skilled laboratory personnel are not required to conduct the analysis.

The present apparatus can be in the form of a completely portable unit which may be operated from a 12V power supply. The present apparatus can also be operated using a mains power supply in the laboratory. The use of recirculated chilled water contributes to the ability of the apparatus to be self contained. Such portability and self containment is not practical with conventional wet chemistry techniques.

The ability to constantly monitor $H_2S$ evolution and to detect when such evolution ceases also offers significant advantages over wet chemical analytical techniques in which a sample is digested for a set period of time. The present inventors have observed that for some samples, digestion can be completed in about 10 minutes as compared to the standard time of one hour allowed for reaction. Thus by monitoring completion of the reaction, the speed of analysis can be considerably increased.

The present invention also provides a method and apparatus for selectively measuring the reduced inorganic sulfur without interference from organic sulfur and sulfate materials. Still further, the acid volatile sulfur fraction can be selectively measured. Also, by monitoring the rate of hydrogen sulfide evolution, important information can be obtained as to the relative amounts of different types of reduced inorganic sulfur in the sample.

It will be appreciated that various changes and modifications may be made to the embodiments as described and claimed herein without departing from the spirit and scope of the invention.

The invention claimed is:

1. A portable apparatus for in-field and laboratory measurement of reduced inorganic sulfur content of a sample comprising: a reaction chamber for receiving a sample to be analysed and a selective reducing agent or a precursor of a selective reducing agent that selectively converts the reduced inorganic sulfur of a sample in the reaction chamber to hydrogen sulfide, an acid reservoir for holding an acid for supply to the reaction chamber, detection means for continuously measuring the amount of hydrogen sulfide evolved by reaction of the selective reducing agent with the sample during said reaction, said detection means being selected from the group consisting of a colourimetric detector, an electrochemical gas analyzer, a UV spectrometer and an IR spectrometer, a conduit for supplying hydrogen sulfide evolved in the reaction chamber to the detection means, a controller for controlling operation of the apparatus, said controller controlling (a) operation of the detection means during analysis of the sample so as to measure hydrogen sulfide evolved on a real time basis as a function of time, and (b) calculation of the cumulative concentration of hydrogen sulfide as a function of hydrogen sulfide concentration and flow rate, and a trap for selectively removing hydrogen sulfide from an exit gas stream leaving the apparatus.

2. An apparatus as set forth in claim 1 further comprising a conduit connecting the acid reservoir to the reaction chamber and wherein said controller controls transfer of acid from the acid reservoir to the reaction chamber such that a predetermined amount of acid is supplied to the reaction chamber.

3. An apparatus as set forth in claim 1 further comprising signaling device for signaling when evolution of hydrogen sulfide has ceased or reduced below a predetermined level.

4. An apparatus as set forth in claim 3 wherein the detection means detects when evolution of hydrogen sulfide has ceased or reduced below a predetermined level and whereafter the controller issues a signal to an operator to signal that the evolution of hydrogen sulfide has ceased or reduced below a predetermined level.

5. An apparatus as set forth in claim 1 further comprising a pump for delivering acid from the acid reservoir to the reaction chamber, and wherein operation of the pump is controlled by the controller.

6. An apparatus as set forth in claim 1 further comprising a heater for heating the reaction chamber.

7. An apparatus as set forth in claim 6 wherein operation of the heater is controlled by the controller.

8. An apparatus as set forth in claim 1 further comprising a source of inert or non-reactive gas for supply to the reaction chamber, and a conduit for supplying the inert or non-reactive gas to the reaction chamber.

9. An apparatus as set forth in claim 8 wherein the inert or non-reactive gas carries evolved hydrogen sulfide from the reaction chamber to the detection means.

10. An apparatus as set forth in claim 8 wherein supply of the inert or non-reactive gas to the reaction chamber is controlled by the controller.

11. An apparatus as set forth in claim 1 wherein the selective reducing agent is selected from the group consisting of Cr(II), and Sn(II).

12. An apparatus as set forth in claim 11 wherein the selective reducing agent is acidified chromous chloride and the selective reducing agent is formed by mixing chromous chloride with hydrochloric acid in the reaction chamber.

13. A portable apparatus for in-field and laboratory measurement of reduced inorganic sulfur content of a sample comprising: a reaction chamber for receiving a sample to be analysed and a selective reducing agent or a precursor of a selective reducing agent that selectively converts the reduced inorganic sulfur of a sample in the reaction chamber to hydrogen sulfide, an acid reservoir for holding an acid, a conduit means connecting the acid reservoir to the reaction chamber, a heater for heating the reaction chamber, a detector for continuously measuring the amount of hydrogen sulfide evolved by reaction of the selective reducing agent with the sample during said reaction, a conduit for supplying hydrogen sulfide evolved in the reaction chamber to the detector, a source of inert or non-reactive gas for supply to the reaction chamber and a conduit for supplying the inert or non-reactive gas to the reaction chamber, a trap for selectively removing hydrogen sulfide from an exit gas stream leaving the apparatus, and a computer for controlling operation of the apparatus, said computer being operative, upon initiation of an analysis by an operator, to transfer acid from the acid reservoir to the reaction chamber, to initiate operation of the heater, to initiate operation of the detector, to monitor a level of evolution of hydrogen sulfide from the reaction chamber and to initiate supply of the inert or non-reactive gas to the reaction chamber, so as to measure hydrogen sulfide evolved on a real time basis as a function of time, said computer being further operative, upon detection that evolution of hydrogen sulfide has ceased or decreased to below a predetermined level, to turn off the heater, to disengage the detector, to interrupt the supply of inert or non-reactive gas and to signal that evolution of hydrogen sulfide has ceased or decreased to below a predetermined level.

14. An apparatus as set forth in claim 13 wherein the selective reducing agent is selected from the group consisting of Cr(II), Sn(II) and Hg(II).

15. An apparatus as set forth in claim 14 wherein the selective reducing agent is acidified chromous chloride and the selective reducing agent is formed by mixing chromium with hydrochloric acid in the reaction chamber.

16. An apparatus as set forth in claim 13 wherein the inert or non-reactive gas is nitrogen.

17. An apparatus as set forth in claim 13 wherein, upon initiation of an analysis run by an operator, the computer is operative to sequentially initiate supply of the inert or non-reactive gas to the reaction chamber to purge the apparatus, initiate transfer of acid from the acid reservoir to the reaction chamber, and initiate operation of the heater, said computer also initiating operation of the detector.

18. An apparatus as set forth in claim 13 further comprising a condenser interposed between the reaction chamber and the detector, and a coolant supply for supplying coolant to the condenser, and wherein the computer controls supply of coolant to the condenser.

19. An apparatus as set forth in claim 13 wherein said detector is selected from the group consisting of a colourimetric detector, a turbidimetric detector, a gravimetric detector, an electrochemical gas analyzer, a UV spectrometer and an IR spectrometer.

* * * * *